United States Patent
Rajaiah et al.

(10) Patent No.: US 6,677,391 B1
(45) Date of Patent: Jan. 13, 2004

(54) TARTAR CONTROL DENTURE ADHESIVE COMPOSITIONS

(75) Inventors: Jayanth Rajaiah, Loveland, OH (US); Kimberly Ann Gilday-Weber, Cincinnati, OH (US); Lisa Catron Ernst, Cincinnati, OH (US); William Michael Glandorf, Mason, OH (US); Donald James White, Jr., Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 435 days.

(21) Appl. No.: 09/716,810

(22) Filed: Nov. 20, 2000

Related U.S. Application Data

(60) Provisional application No. 60/169,702, filed on Dec. 8, 1999.

(51) Int. Cl.$^7$ .................................................. A61K 6/08
(52) U.S. Cl. ........................ 523/120; 523/118; 526/240; 526/432; 526/433; 526/436; 442/286; 442/290; 442/291; 442/299; 424/57
(58) Field of Search ................................. 523/120, 118; 526/240, 432, 433, 436; 442/286, 290, 291, 299; 424/57

(56) References Cited

U.S. PATENT DOCUMENTS

| | | | |
|---|---|---|---|
| 3,429,963 A | 2/1969 | Shedlovsky | 424/56 |
| 3,941,772 A | 3/1976 | Ploger et al. | 260/239 |
| 3,960,888 A | 6/1976 | Ploger et al. | 260/326.5 |
| 3,988,443 A | 10/1976 | Ploger et al. | 424/200 |
| 4,138,477 A | 2/1979 | Gaffar | 424/52 |
| 4,315,779 A | 2/1982 | Heyd et al. | 106/35 |
| 4,627,977 A | 12/1986 | Gaffar et al. | 424/52 |
| 5,096,699 A | 3/1992 | Gaffar et al. | 424/49 |
| 5,192,362 A | 3/1993 | Harvey et al. | 106/35 |
| 5,208,009 A | 5/1993 | Gaffar et al. | 424/49 |
| 5,334,375 A | 8/1994 | Nabi et al. | 424/52 |
| 5,368,844 A | 11/1994 | Gaffar et al. | 424/49 |
| 5,750,591 A | 5/1998 | Clarke et al. | 523/120 |
| 5,753,723 A | 5/1998 | Chang et al. | 523/120 |
| 6,069,188 A * | 5/2000 | Rajaiah et al. | 523/120 |

FOREIGN PATENT DOCUMENTS

| | | | |
|---|---|---|---|
| DE | 2229446 | 12/1972 | A61K/7/16 |
| WO | WO 94/00103 A1 * | 1/1994 | A61K/7/16 |
| WO | WO 99/18140 | 4/1999 | C08F/222/04 |
| WO | WO 99/42079 | 8/1999 | A61K/6/00 |
| WO | WO 00/00165 | 1/2000 | A61K/7/16 |

OTHER PUBLICATIONS

Wilson, M, et al; Prevention of Bacterial Adhesion to Denture Acrylic, 1989, Journal of Dentistry—17: No.4 p. 166–170.

* cited by examiner

Primary Examiner—David W. Wu
Assistant Examiner—Satya Sastri
(74) Attorney, Agent, or Firm—Betty J. Zea

(57) ABSTRACT

The present invention relates to a non-aqueous denture adhesive composition comprising a safe and effective adhesive amount of a denture adhesive; a safe and effective amount of an anticalculus agent; and a non-aqueous denture adhesive carrier; wherein the anticalculus agent is a material effective in reducing calcium phosphate mineral deposition related to calculus formation. The present invention further relates to a method of delivering an anticalculus agent to the oral cavity and teeth, by applying the above composition to dentures, directly to the oral cavity, or applying it to both, and thereafter securing the dentures to the oral cavity.

18 Claims, No Drawings

TARTAR CONTROL DENTURE ADHESIVE COMPOSITIONS

This application claims the benefit of U.S. Provisional Application No. 60/169,702, filed Dec. 8, 1999.

BACKGROUND OF THE INVENTION

Ordinary removable dentures, dental plates and the like, comprise teeth mounted in a suitable plate or base. Denture stabilizers are used to fill the interstices between the dentures and the gums or tissues. Prior to placement of the denture in the oral cavity, a denture stabilizer is applied to the denture-plate surface which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Considerable effort has been made over the years to develop improved denture adhesive compositions. Both synthetic and natural polymers and gums have been used alone, in combination, and in combination with various adhesives and other materials in an attempt to improve hold and reduce oozing of the adhesive from under the dental plate, messiness and difficulty of removing the residual adhesive from the mouth and dentures. For example, alkyl vinyl ether-maleic copolymers and salts thereof are known for providing good hold in denture adhesive compositions. Such disclosures include: U.S. Pat. No. 3,003,988, Germann et al., issued Oct. 10, 1961; U.S. Pat. No. 4,980,391, Kumar et al., issued Dec. 25, 1990; U.S. Pat. No. 5,073,604, Holeva et al., issued Dec. 17, 1991; U.S. Pat. No. 5,525,652, Clarke, issued Jun. 11, 1996; U.S. Pat. No. 5,340,918, Kittrell et al., issued Aug. 23, 1994; U.S. Pat. No. 5,830,933, Synodis et al., issued Nov. 3, 1998.

In addition to adhesion, it is desirable to deliver anticalculus or antitartar benefits in a denture adhesive composition especially for those denture wearers who still have some natural teeth remaining. Tartar is a deposit which forms on the surfaces of teeth. Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris, and microorganisms.

It is generally known that certain polyphosphates are effective anticalculus agents when delivered to the oral cavity by incorporation into aqueous based compositions like dentifrice or mouth rinse compositions. For example U.S. Pat. No. 5,096,699, issued Mar. 17, 1992, Gaffar et al, assigned to Colgate, teaches dentifrice and mouth rinse compositions comprising azacycloalkane-2,2-diphosphonic acids (AAP) and salts thereof and a synthetic anionic polymeric polycarboxylate (SAPP). In addition, U.S. Pat. No. 4,913,895, Miyake et al., issued Apr. 3, 1990, teaches dentifrice and mouth rinse compositions with selected polyphosphates and menthol, anethol, or mixtures. These references, however, only disclose the delivery of polyphosphates via aqueous dentifrice and mouth rinse compositions, where the delivery is also dependent, at least in part, on brushing or rinsing of the oral cavity. The prior art, then, does not suggest that anticalculus agents would be available and delivered in sufficient quantities to render an anticalculus benefit, when placed in a non-aqueous composition, also comprising adhesive components.

Despite the above-noted technologies, as well as others, a need still exists for denture stabilizing compositions providing both superior hold and anticalculus (or antitartar) benefits to the denture wearer. In accordance with the present invention, denture adhesive compositions comprising a denture adhesive component combined with an anticalculus agent provide anticalculus benefits, while providing superior denture hold.

SUMMARY OF THE INVENTION

The present invention relates to a non-aqueous denture adhesive composition comprising:

(a) a safe and effective adhesive amount of a denture adhesive component;

(b) a safe and effective amount of an anticalculus agent selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof; and (c) a non-aqueous denture adhesive carrier.

DETAILED DESCRIPTION OF THE INVENTION

A detailed description of essential and optional components of the present invention is given below.

Definitions

The term "anticalculus" or "antitartar" agent, as used herein, means a material effective in reducing, controlling, inhibiting, preventing, and/or minimizing mineral (e.g., calcium phosphate) deposition related to calculus or tartar formation. The term "safe and effective adhesive amounts" as used herein means an amount sufficient to provide adherence to the oral cavity and/or provide adherence of a dental prosthesis to the oral cavity, without toxicity to the user or damage to oral tissue.

By "safe and effective amount", as used herein, is meant an amount of an agent (e.g., anticalculus agent) high enough to significantly (positively) modify the condition to be treated, but low enough to avoid serious side effects (at a reasonable benefit/risk ratio), within the scope of sound medical/dental judgment. The safe and effective amount of an agent (e.g., anticalculus agent) may vary with the particular condition being treated, the age and physical condition of the patient being treated, the severity of the condition, the duration of treatment, the nature of concurrent therapy, the specific form of the source employed, and the particular vehicle from which the agent is applied.

The term "AVE/MA" as used herein refers to alkyl vinyl ether-maleic acid or anhydride copolymer. The term "AVE/MA/IB" refers to terpolymers with alkyl vinyl ether, maleic acid or anhydride, and isobutylene. The term "mixed polymer salts" or "mixed salts", as used herein, refers to salts of AVE/MA and/or salts of AVE/MA/IB where at least 2 different cations are mixed on the same polymer with each other or with other salts.

The term "free acid" or "FA" component, as used herein, refers either to the unreacted carboxyl groups (—COOH) of AVE/MA copolymer and/or AVE/MA/IB plus any other monovalent cations of carboxyl groups (e.g., COONa) of the polymer. Monovalent cations include Group IA cations, such as sodium, potassium, hydrogen, etc. Preferably, the term "free acid" refers to the unreacted carboxyl groups (—COOH) of AVE/MA and/or AVE/MA/IB plus sodium and potassium cations. More preferably, the term "free acid" refers only to the unreacted carboxyl groups (—COOH) of the AVE/MA and/or AVE/MA/IB.

The percentages used herein to describe the cationic salt function of the alkyl vinyl ether-maleic acid or anhydride copolymers are defined as the stoichiometric percent of the total initial carboxyl groups reacted on the polymer.

All other percentages used herein are by weight of the composition unless otherwise indicated.

Denture Adhesive Components

The present invention comprises a safe and effective adhesive amount of a denture adhesive component, generally at a level of from about 10% to about 90%, in another embodiment from about 15% to about 70%, and in another embodiment from about 20% to about 50%, by weight of the composition. In one embodiment the compositions of the present invention comprise at least 20 percent by weight, and in another embodiment at least 30 percent by weight of the composition, of a denture adhesive component.

"Denture adhesive components" include natural gums, synthetic polymeric gums, AVE/MA, salts of AVE/MA, AVE/MA/IB, salts of AVE/MA/IB, copolymer of maleic anhydride and ethylene and salts thereof, copolymer of maleic anhydride and styrene and salts thereof, copolymer of maleic anhydride and isobutylene and salts thereof, polyacrylic acid and polyacrylates thereof, synthetic polymers, mucoadhesive polymers, water-soluble hydrophilic colloids or polymers having the property of swelling upon exposure to moisture to form a mucilaginous mass, hydrophilic polymers, saccharide derivatives, cellulose derivatives, any adhesive material employed in denture stabilizing compositions, and mixtures thereof. Examples of such materials include karaya gum, guar gum, gelatin, algin, sodium alginate, tragacanth, chitosan, polyethylene glycol, polyethylene oxide, acrylamide polymers, carbopol, polyvinyl alcohol, polyamines, polyquarternary compounds, ethylene oxide polymers, polyvinylpyrrolidone, cationic polyacrylamide polymers, AVE/MA, AVE/MA/IB, mixed salts of AVE/MA, mixed salts of AVE/MA/IB, and mixtures thereof.

In one embodiment the adhesives are salts of AVE/MA, salts of AVE/MA/IB, mixed salts of AVE/MA, mixed salts of AVE/MA/IB, cellulose derivatives, polyethylene glycol, polyethylene oxide, karaya gum, sodium alginate, chitosan, polyvinyl alcohol, and mixtures thereof. In yet another embodiment the adhesives are mixed salts of AVE/MA and cellulose derivatives such as methylcellulose, carboxymethylcellulose, hydroxyethylcellulose, hydroxypropylcellulose, hydroxy-propylmethylcellulose, and mixtures thereof.

Alkyl Vinyl Ether-maleic Copolymer

In one embodiment of the invention the denture adhesive is AVE/MA or salts of AVE/MA. The alkyl vinyl ether-maleic acid co-polymer comprises or consists essentially of the repeated structural unit:

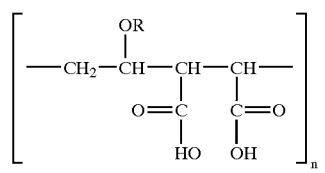

(I)

wherein R represents an alkyl radical, preferably a $C_1$ to $C_5$ alkyl radical, n is an integer greater than one representing the number of repeated occurrences of the structural unit in a molecule of the polymer.

In one embodiment, the adhesive component is AVE/MA and salts thereof, preferably mixed salts of AVE/MA, wherein the copolymer contains a cationic salt function comprising a cation selected from the group consisting of Group 1A and Group 2A cations of the periodic table, yttrium, titanium, zirconium, vanadium, chromium, manganese, iron, nickel, copper, zinc, boron, aluminum, cations and mixtures thereof. In another embodiment, the adhesive component is a mixed salt of AVE/MA containing a cationic salt function comprising a cation selected from the group consisting of strontium, zinc, iron, boron, aluminum, vanadium, chromium, manganese, nickel, copper, yttrium, titanium, magnesium, calcium, sodium, cations and mixtures thereof, and in yet another embodiment the cation is selected from the group consisting of strontium, zinc, iron, magnesium, calcium, sodium, cations, and mixtures thereof.

AVE/MA contains, in one embodiment, a cationic salt function comprising from about 5% to about 50%, in another embodiment, from about 10% to about 40%, in yet another embodiment, from about 10% to about 35% (of the total initial carboxyl groups reacted) zinc cations. These zinc cations can be mixed with other cations selected from the group consisting of: from about 5% to about 65%, preferably from about 10% to about 60%, strontium cations, from about 0.001% to about 2.5%, preferably from about 0.01% to about 2% of iron, boron, aluminum, vanadium, chromium, manganese, nickel, copper, yttrium, and/or titanium cations, from about 5% to about 65%, preferably from about 15% to about 50% of calcium and/or magnesium cations.

AVE/MA and salts thereof and AVE/MA/IB and salts thereof, are also described in U.S. Pat. No. 5,073,604 to Holeva et al., issued Dec. 17, 1991; U.S. Pat. No. 5,525,652, issued Jun. 11, 1996, Clarke et al.; U.S. Pat. No. 4,758,630, issued Jul. 19, 1988, Shah et al.; U.S. Pat. No. 5,304,616, issued Apr. 19, 1994, Rajaiah et al.; U.S. Pat. No. 5,424,058, issued Jun. 13, 1995, Rajaiah; U.S. Pat. No. 5,424,058, issued Jun. 13, 1995, Rajaiah et al.; U.S. Pat. No. 4,758,630, issued Jul. 19, 1988, Shah et al.; U.S. Pat. No. 5,830,933, issued Nov. 3, 1998, Synodis et al.; U.S. Pat. No. 2,047,398, issued Jul. 14, 1936, Voss et al.; U.S. Pat. No. 3,003,988, issued Oct. 10, 1961, Germann et al.; U.S. Pat. No. 5,880,172, Rajaiah et al., issued Mar. 9, 1999; U.S. Pat. No. 5,900,470, Prosise et al., issued May 4, 1999; U.S. Pat. No. 5,037,924, Tazi et al., issued Aug. 6, 1991; U.S. PAt. No. 5,082,913, Tazi et al, issued Jan. 21, 1992; all of which are incorporated herein by reference in their entirety. Salts of AVE/MA are also described in P&G copending applications Ser. No.: 06/152,158, filed Sep. 2, 1999, Rajaiah et al.; Ser. No. 60/129,164, filed Apr. 14, 1999, Rajaiah et al.; Ser. No. 60/129,162, filed Apr. 14, 1999, Rajaiah et al.; Ser. No. 60/152,122, filed Sep. 2, 1999, Rajaiah et al.; Ser. No. 09/291,554, filed Apr. 14, 1999, Rajaiah et al.; Ser. No. 09/389,209, filed Sep. 2, 1999, Rajaiah et al.; and Ser. No. 09/389,210, filed Sep. 2, 1999, Rajaiah et al., all of which are incorporated herein by reference in their entirety.

In one embodiment the free acid level of the salts of the AVE/MA or AVE/MA/IB is at least about 36%, in another embodiment is from about 36% to about 60%, and even in another embodiment is from about 40% to about 55%, of the total initial carboxyl groups of the copolymer or terpolymer.

The specific viscosity of the starting copolymer acid or copolymer anhydride is from about 1.2 to about 14, when preferably measured in a 1% weight/volume solution in MEK (methyl ethyl ketone) at 25° C. Other methods and solvents can be used to measure the specific viscosity such as a 1% weight/volume solution in DMF (dimethyl formamide) at 25° C. and a 1% weight/volume solution in 2-butanone at 25° C.

Suitable AVE/MA copolymers may be prepared by well-known methods of the prior art; see, for example, U.S. Pat. No. 2,782,182, and U.S. Pat. No. 2,047,398, both of which are incorporated by reference herein in their entirety.

The salt form of the subject polymers may be prepared by the interaction of the acid or anhydride polymer with at least one cationic salt function as described above, having a functional group typical of reactants of a carboxylic acid, such as, for example, the hydroxide, oxide, acetate, halide, lactate, etc. in an aqueous medium. In one embodiment, the zinc oxide, strontium carbonate, iron sulfate n-hydrate, etc. are utilized.

Ions that form toxic, irritating or contaminating by-products should be avoided, or special precautions and treatment provided to assure the removal and absence of such by-products from the polymeric salt end-product. The particular compound used should be substantially pure to assure obtaining a substantially pure, polymeric salt end-product.

The salt form of the polymer can be made by mixing the salts (sodium hydroxide, zinc oxide, strontium carbonate, ferric sulfate n-hydrate, calcium hydroxide and/or magnesium oxide, etc.) in an aqueous dispersion. This is combined with the powder alkyl vinyl ether-maleic acid or anhydride copolymer, in the form of a slurry, in an amount sufficient to provide the desired cationic content desired in the end-product. This is done at ambient temperature and then slowly heated to 70°–95° C. with continuous vigorous mixing so as to prevent localized precipitation of the cationic polymeric salt; mixing is continued to ensure that all the salt forming compound is reacted with the copolymer.

Alternatively, the AVE/MA copolymer is hydrolyzed and neutralized in an aqueous mixture or slurry of one or more divalent and/or monovalent metal bases by heating the copolymer/base mixture to a temperature ranging from about 45° C. to about 100° C.

In either of the above processes, the resulting slurry or solution is transferred to shallow stainless steel drying trays and placed in a forced air mechanical convection oven at 60–70° C. for a time sufficient to evaporate the reaction medium (water) and remove water from the copolymer (about 18–24 hours). Alternatively, the resulting slurry or solution can be drum-dried at 100° to 200° C. with hot steam to evaporate the water content and recover the copolymer in the flake form. After drying, the polymer forms brittle flakes which can easily be peeled off from the trays or drum surface and ground to a fine powder as desired to provide satisfactory denture stabilizing properties. Methods of making these mixed salts of AVE/MA polymers are further disclosed in U.S. Pat. No. 5,073,604, Holeva et al., issued Dec. 17, 1991 and U.S. Pat. No. 5,872,161, Liang et al., issued Feb. 16, 1999, both of which are herein incorporated by reference in their entirety.

The Anticalculus Agent

The present compositions comprise a safe and effective amount of at least one anticalculus agent. This amount is generally from about 0.01% to about 40% by weight of the composition, in another embodiment is from about 0.1% to about 25%, and in yet another embodiment is from about 4.5% to about 20%, and in yet another embodiment is from about 5% to about 15%, by weight of the composition. An effective amount of the anticalculus agent is released from the denture adhesive composition. The anticalculus agent should also be essentially compatible with the other components of the composition.

The anticalculus agent is selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof. In one embodiment, the salts are alkali metal salts. In another embodiment the anticalculus agent is selected from the group consisting of polyphosphates and salts thereof; diphosphonates and salts thereof; and mixtures thereof.

Polyphosphate

In one embodiment of the present invention, the anticalculus agent is a polyphosphate. A polyphosphate is generally understood to consist of two or more phosphate molecules arranged primarily in a linear configuration, although some cyclic derivatives may be present. Linear polyphosphates correspond to $(X\,PO_3)_n$ where n is about 2 to about 125, wherein preferably n is greater than 4, and X is for example sodium, potassium, etc. For $(X\,PO_3)_n$ when n is at least 3 the polyphosphates are glassy in character. Counterions for these phosphates may be the alkali metal, alkaline earth metal, ammonium, $C_2$–$C_6$ alkanolammonium and salt mixtures. Polyphosphates are generally employed as their wholly or partially neutralized water soluble alkali metal salts such as potassium, sodium, ammonium salts, and mixtures thereof. The inorganic polyphosphate salts include alkali metal (e.g. sodium) tripolyphosphate, tetrapolyphosphate, dialkyl metal (e.g. disodium) diacid, trialkyl metal (e.g. trisodium) monoacid, potassium hydrogen phosphate, sodium hydrogen phosphate, and alkali metal (e.g. sodium) hexametaphosphate, and mixtures thereof. Polyphosphates larger than tetrapolyphosphate usually occur as amorphous glassy materials. In one embodiment the polyphosphates are those manufactured by FMC Corporation which are commercially known as Sodaphos (n≈6), Hexaphos (n≈13), and Glass H (n≈21), and mixtures thereof. The polyphosphate source will typically comprise from about 0.5% to about 20%, in one embodiment from about 4% to about 15%, in yet another embodiment from about 6% to about 12%, by weight of the composition.

The phosphate sources are described in more detail in Kirk & Othmer, *Encyclopedia of Chemical Technology*, Fourth Edition, Volume 18, Wiley-Interscience Publishers (1996), pages 685–707, incorporated herein by reference in its entirety, including all references incorporated into Kirk & Othmer.

In one embodiment the polyphosphates are the linear "glassy" polyposphates having the formula:

$$XO(XPO_3)_nX$$

wherein X is sodium or potassium; and n averages from about 6 to about 125.

In one embodiment, when n is at least 2 in either of the above polyphosphate formulas, the level of anticalculus agent is from about 4.5% to about 40%, in another embodiment is from about 5% to about 25%, and in even another embodiment is from about 8% to about 15%, by weight of the composition. Polyphosphates are disclosed in U.S. Pat. No. 4,913,895, herein incorporated by reference.

Pyrophosphate

The pyrophosphate salts useful in the present compositions include, alkali metal pyrophosphates, di-, tri-, and mono-potassium or sodium pyrophosphates, dialkali metal pyrophosphate salts, tetraalkali metal pyrophosphate salts, and mixtures thereof. In one embodiment the pyrophosphate salt is selected from the group consisting of trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof. The pyrophosphate salts described in U.S. Pat. No. 4,515,772, issued May 7, 1985, and U.S. Pat. No. 4,885,155, issued Dec. 5, 1989, both to Parran et al., are incorporated herein by reference in their entirety, as well as the references disclosed therein. The pyrophosphate salts are described in more detail in Kirk & Othmer, *Encyclopedia of Chemical Technology*, Third Edition, Volume 17, Wiley-Interscience Publishers (1982), pages 685–707, incorporated herein by reference in its entirety, including all references incorporated into Kirk & Othmer.

In one embodiment, the compositions of the present invention comprise tetrasodium pyrophosphate. Tetrasodium pyrophosphate may be the anhydrous salt form or the decahydrate form, or any other species stable in solid form in the present compositions. The salt is in its solid particle form, which may be its crystalline and/or amorphous state, with the particle size of the salt preferably being small enough to be aesthetically acceptable and readily soluble during use.

The level of pyrophosphate salt in the compositions of the present invention is any safe and effective amount, and is generally from about 1.5% to about 15%, in another embodiment from about 2% to about 10%, and yet in another embodiment from about 3% to about 8%, by weight of the composition.

Other Anticalculus Agents

Polyolefin sulfonates include those wherein the olefin group contains 2 or more carbon atoms, and salts thereof. Polyolefin phosphonates include those wherein the olefin group contains 2 or more carbon atoms. Polyvinylphosphonates include polyvinylphosphonic acid. Diphosphonates and salts thereof include azocycloalkane-2,2-diphosphonic acids and salts thereof, ions of azocycloalkane-2,2-diphosphonic acids and salts thereof (such as those which the alkane moiety has five, six or seven carbon atoms, in which the nitrogen atom is unsubstituted or carries a lower alkyl substitutent, e.g. methyl), azacyclohexane-2,2-diphosphonic acid, azacyclopentane-2,2-diphosphonic acid, N-methyl-azacyclopentane-2,3-diphosphonic acid, EHDP (ethanehydroxy-1,1,-diphosphonic acid), AHP (azacycloheptane-2,2-diphosphonic acid, a.k.a. 1-azocycloheptylidene-2,2-diphosphonic acid), ethane-1-amino-1,1-diphosphonate, dichloromethane-diphosphonate, etc. Phosphonoalkane carboxylic acid or their alkali metal salts include PPTA (phosphonopropane tricarboxylic acid), PBTA (phosphonobutane-1,2,4-tricarboxylic acid), each as acid or alkali metal salts. Polyolefin phosphates include those wherein the olefin group contains 2 or more carbon atoms. Polypeptides include polyaspartic and polyglutamic acids.

Azacycloalkane-2,2-diphosphonic acids are disclosed in U.S. Pat. No. 3,941,772, issued Mar. 2, 1976, Ploger et al., assigned to Henkel and U.S. Pat. No. 3,988,443, issued Oct. 26, 1976, Ploger et al., which are herein incorporated by reference in their entirety.

Non-aqueous Denture Adhesive Carrier

The non-aqueous denture adhesive carrier is selected from the group consisting of a non-aqueous vehicle and a non-adhesive self supporting layer. The level of non-aqueous vehicle is from 10% to about 90%, in another embodiment is from about 20% to about 80%, and in yet another embodiment is from about 20% to about 60%, by weight of the composition.

Non-aqueous Vehicles

The non-aqueous vehicle is generally any chemical in any physical form that does not contain water. The non-aqueous vehicle is selected from the group consisting of liquid petrolatum, petrolatum, mineral oil, glycerin, natural and synthetic oils, fats, silicone and silicone derivatives, polyvinylacetate, natural and synthetic waxes such as animal waxes like beeswax, lanolin and shellac, hydrocarbons, hydrocarbon derivatives, vegetable oil waxes such as carnauba, candelilla and bayberry wax, vegetable oils such as caprylic/capric triglycerides, in another embodiment is selected from the group consisting of liquid petrolatum, petrolatum, mineral oil, vegetable oils such as corn, soy bean, cottonseed, castor, palm and coconut oils and animal oil such as fish oil and oleic acid, and mixtures thereof; and in yet another embodiment is mineral oil.

Caprylic/capric triglycerides are triglycerides of medium chain fatty acids where the —C═O—R group is 8–10 carbons and is obtained by the addition of glycerol to a mixture of capric and caprylic acids:

Caprylic acid: $CH_3(CH_2)_6CO_2H$

Capric acid: $CH_3(CH_2)_8CO_2H$

Therefore, vegetable oils comprised of saturated medium chain fatty acids such as caprylic acid, capric acid and mixtures thereof, can be used in the present invention. These vegetable oils and other non-aqueous vehicles for denture adhesive compositions are further described in U.S. Pat. No. 5,561,177, issued on Oct. 1, 1996, Khaledi et al., which is incorporated herein by reference in its entirety.

Non-adhesive Self-supporting Layer

The non-aqueous carrier can comprise at least one non-adhesive self-supporting layer. The non-adhesive self-supporting layer is characterized by its ability to maintain strength and provide integrity for the adhesive composition in the presence of water and/or saliva. The non-adhesive self-supporting layer may include materials such as polyester, polypropylene, nylon, rayon, cellulose acetate, non-adhesive cellulose derivatives, cloth, fibrous fleece, paper, plastic, leather, microcrystalline wax, synthetic fibers, natural fibers, and mixtures thereof. Preferred are non-adhesive cellulose derivatives, polyester, polypropylene, nylon, rayon, cloth, paper, microcrystalline wax, and mixtures thereof. More preferred are polyester, polypropylene, rayon, nylon, cloth and paper.

The non-adhesive self-supporting layer may be in any physical form suitable for providing strength and/or integrity to the present adhesive compositions. Such physical forms include non-woven, woven, continuous, chopped, foam, and combinations thereof. In addition, the non-adhesive self-supporting layer may be formed by any process commonly known in the art. Such processes include un-bonded, spraybonded, spun-bonded, needle-punched, carded, thermal bonded hydroentangled, meltblown, aperture print bonded, needled, wet-laid, dry-laid, and combinations thereof.

The present denture adhesive compositions which comprise a non-adhesive self-supporting layer may also comprise a coating which is sticky to dry dentures and, if present, will be placed on one side of the denture adhesive composition. Compositions suitable for use as this type of adhesive layer include silicones, rubbers, petrolatum, natural polymers, synthetic polymers, and mixtures thereof. The adhesive layer may be present at a level of from about 0% to about 70%, and in another embodiment from about 0.5% to about 20%, by weight of the composition.

Miscellaneous Carriers

Other suitable ingredients include colorants, preservatives (such as methyl and propyl parabens), thickeners such as silicon dioxide, and polyethylene glycol. Colorants, preservatives, thickeners may be present at levels of from about 0% to about 20%, by weight of the composition.

Plasticizers

In addition one or more toxicologically-acceptable plasticizers may also be included in the present compositions. The term "toxicologically-acceptable", as used herein, is used to describe materials that are suitable in their toxicity profile for administration to humans and/or lower animals. Plasticizers that may be used in the present compositions include dimethyl phthalate, diethyl phthalate, dioctyl phthalate, glycerin, diethylene glycol, triethylene glycol, Igepal®, Gafac®, sorbitol, tricresyl phosphate, dimethyl sebacate, ethyl glycolate, ethylphthalyl ethyl glycolate, o- and p-toluene ethyl sulfonamide, and mixtures thereof. Plasticizers may be present at a level of from about 0% to about 70%, in another embodiment from about 1% to about 30%, by weight of the compositions.

Flavors, Fragrance, Sensates

The compositions of the present invention may also include one or more components which provide flavor, fragrance, and/or sensate benefit (warming or cooling agents). Suitable components include natural or artificial sweetening agents, menthol, menthyl lactate, wintergreen oil, peppermint oil, spearmint oil, leaf alcohol, clove bud oil, anethole, methyl salicylate, eucalyptol, cassia, 1-8 menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal known as CGA, and mixtures thereof, as well as coolants. The coolant can be any of a wide variety of materials. Included among such materials are carboxamides, menthol, ketals, diols, and mixtures thereof. Preferred coolants in the present compositions are the paramenthan carboxyamide agents such as N-ethyl-p-menthan-3-carboxamide, known commercially as "WS-3", N,2,3-trimethyl-2-isopropylbutanamide, known as "WS-23," and mixtures thereof. Additional preferred coolants are selected from the group consisting of menthol, 3-1-menthoxypropane-1,2-diol known as TK-10 manufactured by Takasago, menthone glycerol acetal known as MGA manufactured by Haarmann and Reimer, and menthyl lactate known as Frescolat® manufactured by Haarmann and Reimer. The terms menthol and menthyl as used herein include dextro- and levorotatory isomers of these compounds and racemic mixtures thereof. TK-10 is described in U.S. Pat. No. 4,459,425, Amano et al., issued Jul. 10, 1984. WS-3 and other agents are described in U.S. Pat. No. 4,136,163, Watson, et al., issued Jan. 23, 1979; the disclosure of both are herein incorporated by reference in their entirety. These agents may be present at a level of from about 0% to about 50%, by weight of the composition.

Other Optional Ingredients

The denture adhesive compositions may also be used as a denture adhesive and/or bioadhesive and comprise one or more therapeutic actives suitable for topical administration. Therapeutic actives may be present at a level of from about 0% to about 70%, by weight of the composition, and in one embodiment from about 1% to about 20% by weight of the compostion. Therapeutic actives include antimicrobial agents such as iodine, tricolsan, peroxides, sulfonamides, bisbiguanides, or phenolics; antibiotics such as tetracycline, neomycin, kanamycin, metronidazole, cetylpyridium chloride, or clindamycin; anti-inflammatory agents such as aspirin, acetaminophen, naproxen and its salts, ibuprofen, ketorolac, flurbiprofen, indomethacin, eugenol, or hydrocortisone; dentinal desensitizing agents such as potassium nitrate, strontium chloride or sodium fluoride; fluorides such as sodium fluoride, stannour fluoride, MFP; anesthetic agents such as lidocaine or benzocaine; anti-fungals such as those for the treatment of *candida albicans*; aromatics such as camphor, eucalyptus oil, and aldehyde derivatives such as benzaldehyde; insulin; steroids; herbal and other plant derived remedies; baking soda and anti-neoplastics. It is recognized that in certain forms of therapy, combinations of these agents in the same delivery system may be useful in order to obtain an optimal effect. Thus, for example, an antimicrobial and an anti-inflammatory agent may be combined in a single delivery system to provide combined effectiveness.

Process for Preparation of the Composition

A process for preparing denture adhesive compositions of the present invention (creams, powders, wafers, non-aqueous liquids, aerosols, pastes) comprises conventional methods disclosed in the art. Conventional methods are taught in U.S. Pat. No. 5,525,652, issued Jun. 11, 1996, Clarke et al.; U.S. Pat. No. 3,003,988, issued Oct. 10, 1961, Germann et al.; U.S. Pat. No. 5,073,604, Holeva et al., issued Dec. 17, 1991; and U.S. Pat. No. 5,872,161, Liang et al., issued Feb. 16, 1999, all of which are herein incorporated by reference in their entirety.

A process for the preparation of the present denture adhesive compositions comprising a non-adhesive self-supporting layer, comprises coating a weighed amount of the adhesive components onto the non-adhesive self-supporting layer. This process is disclosed in U.S. Pat. No. 5,877,233, Liang et al, issued Mar. 2, 1999; U.S. Pat. No. 5,872,160, issued Feb. 16, 99, Liang et al.; U.S. Pat. No. 5,880,172, Rajaiah et al., filed Oct. 25, 1996, all of which are incorporated herein by reference in their entirety.

Composition Use

The adhesive compositions may be in the form of a powder, cream, paste, non-aqueous liquid, aerosol, and/or wafer. Cream, paste, and other compositions of the present invention are generally applied to the denture prosthesis and thereafter the denture is secured to the oral cavity, as known in the art.

The following examples further describe and demonstrate embodiments within the scope of the present invention. The examples are given solely for the purpose of illustration and are not to be construed as limitations of the present invention. Many variations of these are possible without departing from the spirit and scope of the invention.

EXAMPLE I

Denture stabilizing compositions in cream form are made by blending together the following ingredients:

| | A Grams | B Grams | C Grams | D Grams | E Grams |
|---|---|---|---|---|---|
| White Mineral Oil | 23.93 | 23.93 | 23.93 | 23.93 | 23.93 |
| Petrolatum, White | 19.8 | 8.87 | 14.37 | 16.87 | 16.87 |
| Carboxymethylcellulose Sodium | 20.00 | 20.00 | 20.00 | 20.00 | 20.00 |
| Silicon Dioxide, Collodial | 1.14 | 1.14 | 1.14 | 1.14 | 1.14 |

-continued

|  | A<br>Grams | B<br>Grams | C<br>Grams | D<br>Grams | E<br>Grams |
|---|---|---|---|---|---|
| Colorant (Opatint Red Dye) | 0.06 | 0.06 | 0.06 | 0.06 | 0.06 |
| Any salt, acid or anyhdride of AVE/MA and/or AVE/MA/IB | 33.00 | 33.00 | 33.00 | 33.00 | 33.00 |
| Tetra Sodium Pyro Phosphate (TSPP) | 2.05 | — | 2.50 | | |
| EHDP (ethanehydroxy-1, 1,-diphosphonic acid) | | | | 5.00 | |
| AHP (azacycloheptane-2, 2-diphosphonic acid) | | | | | 5.00 |
| Poly Phosphate (Glass-H[1]) | — | 13.00 | 5.00 | | |

The red dye, petrolatum, and mineral oil are weighed, heated and mixed in a glass jar at 50 to 60° C. until visually uniform. The powders (colloidal silicon dioxide, CMC, AVE/MA, AVE/MA/IB and TSPP or AHP or EHDP or Glass-H) are then weighed and shake blended together in a container. Thereafter, the powders are mixed into the liquid with a spatula until visually a uniform pink cream. The above compositions can be modified by increasing or decreasing the level of TSPP by 0 to 15 grams, Glass-H by 0 to 15 grams, AVE/MA or AVE/MA/IB by 0 to 15 grams, petrolatum by 0 to 15 grams, and/or the CMC by 0 to 15 grams. The above compositions can also be modified by using any other suitable anticalculus agent. The subject places from 0.1 to 5 grams of the cream composition on the denture. Then the subject inserts the denture into his/her mouth and presses it into place.

EXAMPLE II

Denture stabilizing compositions in powder form are made by blending together the following ingredients:

|  | A | B | C | D | E |
|---|---|---|---|---|---|
| Carboxymethylcellulose Sodium | 20.00 | 20.00 | 20.00 | 20.00 | 20.00 |
| Silicon Dioxide, Colloidal | 1.14 | 1.14 | 1.14 | 1.14 | 1.14 |
| Any salt, acid or anyhdride of AVE/MA and/or AVE/MA/IB | 33.00 | 33.00 | 33.00 | 33.00 | 33.00 |
| Tetra Sodium Pyro Phosphate (TSPP) | 2.05 | — | 2.50 | | |
| EHDP (ethanehydroxy-1,1,-diphosphonic acid) | | | | 5.00 | |
| AHP (azacycloheptane-2,2-diphosphonic acid) | | | | | 5.00 |
| Poly Phosphate (Glass-H[1]) | | 13.00 | 5.00 | | |

[1]Polyphosphate manufactured by FMC Corporation where n=21 (average).

All components are blended together. The above compositions can be modified by increasing or decreasing the level of TSPP by 0 to 15 grams, Glass-H by 0 to 15 grams, AHP by 0 to 15 grams, EHDP by 0 to 15 grams, AVE/MA or AVE/MA/IB by 0 to 15 grams, and/or the CMC by 0 to 15 grams. The above compositions can also be modified by using any other suitable anticalculus agent. The subject places from 0.1 to 5 grams of the composition on a denture and then moistens it. Then the subject inserts the denture into his/her mouth and presses it into place.

EXAMPLE III

Denture stabilizing compositions in wafer form can be made by wetting a 58" by 20" non-woven polyester (non-adhesive self-supporting layer) with water. This wet sheet is uniformly coated with 1 to 3 times the weight of compositions listed above in example-II. Thereafter, the layer is rewetted with water. The layer is dried. The composition is mechanically softened by ring-roller, and then the composition is smoothed on a hydraulic press. The composition is die cut into desired shapes. These wafer compositions are moistened and applied to the dentures. Then the denture is inserted into the mouth and pressed into place.

What is claimed is:

1. A denture adhesive composition comprising:
   a) from about 20% to about 70% by weight of the composition of a denture adhesive component;
   b) from about 0.01% to about 40% of an anticalculus agent selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof; and
   c) a non-aqueous denture adhesive carrier:
      wherein when the anticalculus agent is polyphosphate the level of polyphosphate is from about 4.5% to about 40% by weight of the composition.

2. The composition of claim 1 wherein the denture adhesive component is selected from the group consisting of natural gums, synthetic polymeric gums, AVE/MA, salts of AVE/MA, AVE/MA/IB, salts of AVE/MA/IB, copolymer of maleic anhydride and ethylene and salts thereof, copolymer of maleic anhydride and styrene and salts thereof, copolymer of maleic anhydride and isobutylene and salts thereof, polyacrylic acid and polyacrylates thereof, synthetic polymers, mucoadhesive polymers, water-soluble hydrophilic colloids or polymers having the property of swelling upon exposure to moisture to form a mucilaginous mass, hydrophilic polymers, saccharide derivatives, cellulose derivatives, and mixtures thereof.

3. The composition of claim 2 wherein the denture adhesive component is selected from the group consisting of karaya gum, guar gum, gelatin, algin, sodium alginate, tragacanth, chitosan, polyethylene glycol, acrylamide polymers, carbopol, polyvinyl alcohol, polyamines, polyquarternary compounds, ethylene oxide polymers, polyvinylpyrrolidone, cationic polyacrylamide polymers, salts of AVE/MA and mixtures thereof.

4. The composition of claim 3 wherein the denture adhesive component is a salt of AVE/MA, the salt containing a cationic salt function comprising a cation selected from the group consisting of Group 1A and Group 2A cations of the periodic table, yttrium, titanium, zirconium, vanadium, chromium, manganese, iron, nickel, copper, zinc, boron, aluminum, and mixtures thereof.

5. The composition of claim 4 wherein the cation is selected from the group consisting of strontium, zinc, iron, magnesium, calcium, sodium, and mixtures thereof.

6. The composition of claim 2 wherein the cellulose derivative is selected from the group consisting of bydroxyethylcellulose, hydroxypropylcellulose, hydroxypropylmethyl-cellulose, sodium carboxymethylcellulose, and mixtures thereof.

7. The composition of claim 6 wherein the cellulose derivative is sodium carboxymethylcellulose.

8. The composition of claim 2 wherein the anticalculus agent is selected from the group consisting of polyphosphates and salts thereof; diphosphonates and salts thereof; and mixtures thereof.

9. The composition of claim 1 wherein the non-aqueous denture adhesive carrier is selected from the group consisting of a non-aqueous vehicle and a non-adhesive self supporting layer.

10. The composition of claim 9 wherein the non-aqueous vehicle is selected from the group consisting of liquid petrolatum, petrolatum, mineral oil, glycerin, natural and synthetic oils, fats, silicone and silicone derivatives, polyvinylacetate, natural and synthetic waxes, vegetable oil waxes, vegetable oils, and mixtures thereof.

11. The composition of claim 9 wherein the non-aqueous vehicle is selected from the group consisting of liquid petrolatum, petrolatum, mineral oil, glycerin, and mixtures thereof.

12. The composition of claim 9 wherein the carrier is a non-adhesive self-supporting layer.

13. The composition of claim 12 wherein the non-adhesive self-supporting layer is selected from the group consisting of polyester, polypropylene, nylon, rayon, cellulose acetate, non-adhesive cellulose derivatives, cloth, fibrous fleece, paper, plastic, leather, synthetic fibers, natural fibers, and mixtures, thereof.

14. A method of delivering an anticalculus agent to the oral cavity and teeth, by applying a composition to the dentures, the oral cavity, or both, and thereafter securing a denture prosthesis to the oral cavity, the composition comprising:
    a) from about 15% to about 70% by weight of the composition of a denture adhesive component;
    b) from about 0.01% to about 40% by weight of an anticalculus agent selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof; and
    c) a non-aqueous denture adhesive carrier:
        wherein when the anticalculus agent is polyphosphate the level of polyphosphate is from about 4.5% about 40% by weight of the composition.

15. A powder denture adhesive composition comprising:
    a) a safe and effective adhesive amount of a denture adhesive component;
    b) a safe and effective amount of an anticalculus agent wherein the anticalculus agent is selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof;
wherein the composition is in the form of a powder and when the anticalculus agent is polyphosphate the level of polyphosphate is from about 4.5% to about 40% by weight of the composition.

16. A denture adhesive composition comprising:
    a) from about 20% to about 70% by weight of a denture adhesive component selected from the group consisting of natural gums, synthetic polymeric gums, AVE/MA, salts of AVE/MA, AVE/MA/IB, salts of AVE/MA/IB, copolymer of maleic anhydride and ethylene and salts thereof, copolymer of maleic anhydride and styrene and salts thereof, copolymer of maleic anhydride and isobutylene and salts thereof, polyacrylic acid and polyacrylates thereof synthetic polymers, mucoadhesive polymers, water-soluble hydrophilic colloids or polymers having the property of swelling upon exposure to moisture to form a mucilaginous mass, hydrophilic polymers, saccharide derivatives, cellulose derivatives, and mixtures thereof,
    b) from about 0.01% to about 40% by weight of an anticalulus agent wherein the anticalculus agent is selected from the group consisting of polyposphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof; and
    c) a non-aqueous denture adhesive carrier;
wherein when the anticalculus agent is polyphosphate, the free acid level of the salt of AVE/MA is at least about 36%.

17. A method of reducing, controlling, inhibiting, or preventing calculus or tartar in the oral cavity by applying a composition to the dentures, the oral cavity, or both, and thereafter securing a denture prosthesis to the oral cavity, the composition comprising:
    a) from about 15% to about 70% by weight of the composition of a denture adhesive component;
    b) from about 0.01% to about 40% of an anticalculus agent selected from the group consisting of polyphosphates and salts thereof; polyamino propane sulfonic acid (AMPS) and salts thereof; polyolefin sulfonates and salts thereof; polyvinyl phosphates and salts thereof; polyolefin phosphates and salts thereof; diphosphonates and salts thereof; phosphonoalkane carboxylic acid and salts thereof; polyphosphonates and salts thereof; polyvinyl phosphonates and salts thereof; polyolefin phosphonates and salts thereof; polypeptides; and mixtures thereof; and
    c) a non-aqueous denture adhesive carrier:
wherein when the anticalculus agent is polyphosphate the level of polyphosphate is from about 4.5% to about 40% by weight of the composition.

18. A denture adhesive composition comprising:
    a) from about 15% to about 70% by weight of the composition of a denture adhesive component;
    b) from about 0.01% to about 40% of an anticalculus agent selected from the group consisting of azacycloalkane-2,2-diphosphonic acids, alkali metal pyrophosphates, di-, tri-, and mono-potassium or sodium pyrophosphates, dialkali metal pyrophosphate salts, tetraalkali metal pyrophosphate salts, trisodium pyrophosphate, disodium dihydrogen pyrophosphate ($Na_2H_2P_2O_7$), dipotassium pyrophosphate, tetrasodium pyrophosphate ($Na_4P_2O_7$), tetrapotassium pyrophosphate ($K_4P_2O_7$), and mixtures thereof; and
    c) a non-aqueous denture adhesive carrier:
wherein when the anticalculus agent is polyphosphate the level of polyphosphate is from about 4.5% to about 40% by weight of the composition.

* * * * *